(12) United States Patent
Nakamura

(10) Patent No.: US 9,403,645 B2
(45) Date of Patent: Aug. 2, 2016

(54) MEASURING CONTAINER SUPPLYING DEVICE

(71) Applicant: JEOL Ltd., Tokyo (JP)

(72) Inventor: Mizuki Nakamura, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/768,785

(22) PCT Filed: Feb. 14, 2014

(86) PCT No.: PCT/JP2014/053469
§ 371 (c)(1),
(2) Date: Aug. 19, 2015

(87) PCT Pub. No.: WO2014/012937
PCT Pub. Date: Aug. 28, 2014

(65) Prior Publication Data
US 2016/0001981 A1    Jan. 7, 2016

(30) Foreign Application Priority Data

Feb. 20, 2013  (JP) ................. 2013-031126

(51) Int. Cl.
| | | |
|---|---|---|
| *B65G 47/12* | (2006.01) | |
| *B65G 37/00* | (2006.01) | |
| *G01N 35/04* | (2006.01) | |
| *G01N 35/02* | (2006.01) | |

(52) U.S. Cl.
CPC .............. *B65G 37/00* (2013.01); *G01N 35/021* (2013.01); *G01N 35/04* (2013.01); *G01N 2035/0406* (2013.01); *G01N 2035/0498* (2013.01)

(58) Field of Classification Search
CPC ................................. B65G 37/00; B65G 27/10
USPC ............ 198/774.3, 773, 750.14, 750.15, 443, 198/347.1, 521, 752.1, 766; 193/2 B
See application file for complete search history.

(56) References Cited

U.S. PATENT DOCUMENTS 9,110,043 B2 *   8/2015   Kaneko ............... G01N 35/025
2012/0171078 A1  7/2012   Kaneko

FOREIGN PATENT DOCUMENTS

| GB | 701848 | 1/1954 |
|---|---|---|
| JP | 62289762 A | 12/1987 |
| JP | 4334554 A | 11/1992 |
| JP | 542215 U | 6/1993 |
| JP | 2007309792 A | 11/2007 |
| JP | 200896115 A | 4/2008 |
| JP | 2011209045 A | 10/2011 |
| JP | 2012141226 A | 7/2012 |

* cited by examiner

*Primary Examiner* — Gene Crawford
*Assistant Examiner* — Lester Rushin
(74) *Attorney, Agent, or Firm* — THe Webb Law Firm

(57) ABSTRACT

An alignment transfer section (30) transfers measurement containers (60) that align along an alignment rail (32). A step (66) of each measurement container (60) that is formed by a body and a neck comes in contact with an upper side (32a) of the alignment rail (32). The alignment rail (32) is disposed to slope downward toward the end thereof. The alignment transfer section (30) includes an upthrust plate (34) that comes in contact with the bottom of the measurement containers (60) supported by the alignment rail (32), and transfers the measurement containers (60) toward the end of the alignment rail (32) by causing the upthrust plate (34) or the alignment rail (32) to make an upward-downward motion.

3 Claims, 6 Drawing Sheets

START STATE

UPTHRUST

FALL DOWN

COMPLETION
OF UPTHRUST

MEASURING CONTAINER SUPPLYING DEVICE

CROSS-REFERENCE TO RELATED APPLICATIONS

This application is the United States national phase of International Application No. PCT/JP2014/053469 filed Feb. 14, 2014, and claims priority to Japanese Patent Application No. 2013-031126 filed Feb. 20, 2013, the disclosures of which are hereby incorporated in their entirety by reference.

TECHNICAL FIELD

The present invention relates to a measurement container supply device that is included in an automatic analyzer.

BACKGROUND ART

A sample analyzer that includes a container supply device that supplies a container used to analyze a sample has been known (see JP-A-2012-141226, for example). The container supply device includes a storage section that stores a container, a carry-out section that carries the container out of the storage section, a pair of transfer rails that transfer the container that has been carried by the carry-out section, and a rotary transfer section that transfers the container that has been transferred by the pair of transfer rails to a standby position at which a supply catcher section can hold the container.

SUMMARY OF INVENTION

Technical Problem

The above container supply device is configured so that the container that has been carried by the carry-out section slides down toward the rotary transfer section in a state in which the collar thereof engages with the upper side of the transfer rails. Therefore, when the container is light in weight, the container may not slide down due to friction between the upper side of the transfer rails and the collar. Such problem may be solved by increasing the slope angle of the transfer rails. In this case, however, the height of the container supply device necessarily increases.

The invention was conceived in view of the above problems. Several aspects of the invention may provide a measurement container supply device that can reliably transfer a measurement container supported (held) by an alignment rail.

Summary Of The Invention (1) According to one embodiment of the invention, there is provided a measurement container supply device that is included in an automatic analyzer, the measurement container supply device including:

a storage section that stores a measurement container;

a carry-out section that carries the measurement container out of the storage section;

an alignment transfer section that transfers the measurement container that has been carried by the carry-out section and aligned along an alignment rail toward an end of the alignment rail; and a supply section that holds the measurement container that has been transferred to the end of the alignment rail, and transfers the measurement container to a predetermined supply position, the measurement container including a body, and a neck that has an outer diameter larger than that of the body, a step that is formed by the body and the neck coming in contact with an upper side of the alignment rail so that the measurement container is supported by the alignment rail in a suspended state, the alignment rail being disposed to slope downward toward the end, and the alignment transfer section including a plate-like member that comes in contact with a bottom of the measurement container that is supported by the alignment rail, and transferring the measurement container toward the end of the alignment rail by causing at least one of the plate-like member and the alignment rail to make an upward-downward motion.

According to this embodiment, it is possible to reliably transfer the measurement container supported by the alignment rail by transferring the measurement container toward the end of the alignment rail by causing at least one of the plate-like member (that comes in contact with the bottom of the measurement container that is supported by the alignment rail) and the alignment rail to make an upward-downward motion.

(2) In the above measurement container supply device, the alignment transfer section may cause at least one of the plate-like member and the alignment rail to make an upward-downward motion so that a state in which the step comes in contact with the upper side of the alignment rail and a state in which the step is situated away from the upper side of the alignment rail are alternately repeated.

It is possible to more reliably transfer the measurement container supported by the alignment rail by causing at least one of the plate-like member and the alignment rail to make an upward-downward motion so that a state in which the step of the measurement container comes in contact with the upper side of the alignment rail and a state in which the step of the measurement container is situated away from the upper side of the alignment rail are alternately repeated.

(3) In the above measurement container supply device, the alignment transfer section may cause the plate-like member or the alignment rail to make an upward-downward motion by rotating an eccentric shaft that rotatably supports the plate-like member or the alignment rail.

This makes it possible to cause at least one of the plate-like member and the alignment rail to make an upward-downward motion using a simple configuration.

DESCRIPTION OF EMBODIMENTS

Exemplary embodiments of the invention are described in detail below with reference to the drawings. Note that the following exemplary embodiments do not unduly limit the scope of the invention as stated in the claims. Note also that all of the elements described in connection with the following exemplary embodiments should not necessarily be taken as essential elements of the invention.

1. Overall Configuration

Figure 1:
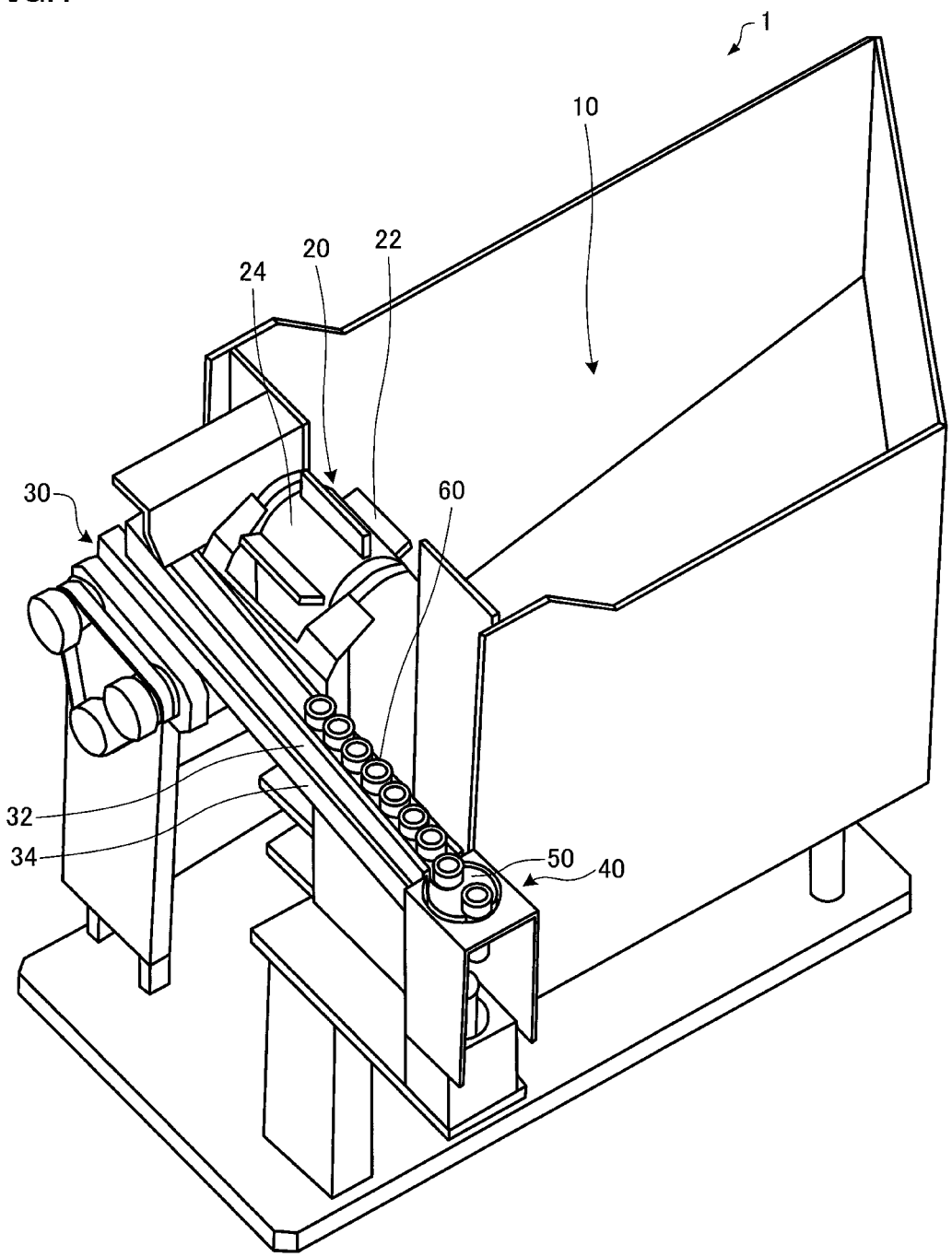
FIG. 1 is a perspective view illustrating an example of a measurement container supply device according to one embodiment of the invention.

FIG. 1 illustrates an example of a measurement container supply device according to one embodiment of the invention. The measurement container supply device according to one embodiment of the invention is a device that is included in an automatic analyzer (i.e., forms part of the automatic analyzer), and supplies a measurement container that is used to analyze a sample.

As illustrated in FIG. 1, a measurement container supply device 1 includes a storage section 10 that stores a plurality of measurement containers 60 placed therein, a carry-out section 20 that carries the measurement container 60 stored in the storage section 10 out of the storage section 10, an alignment transfer section 30 that transfers the measurement container 60 that has been carried by the carry-out section 20 toward a supply section 40, and the supply section 40 that holds the measurement container 60 that has been transferred by the alignment transfer section 30, and transfers the measurement container 60 to a predetermined supply position.

The carry-out section 20 includes a belt 24 that is provided with a plurality of holding plates 22 that can hold the measurement container 60, and a driver section that rotates the belt 24. The measurement container 60 stored in the storage section 10 is held by the holding plate 22, transferred upward due to rotation of the belt 24, and falls from the belt 24 at a position opposite to the storage section 10.

Figure 2:
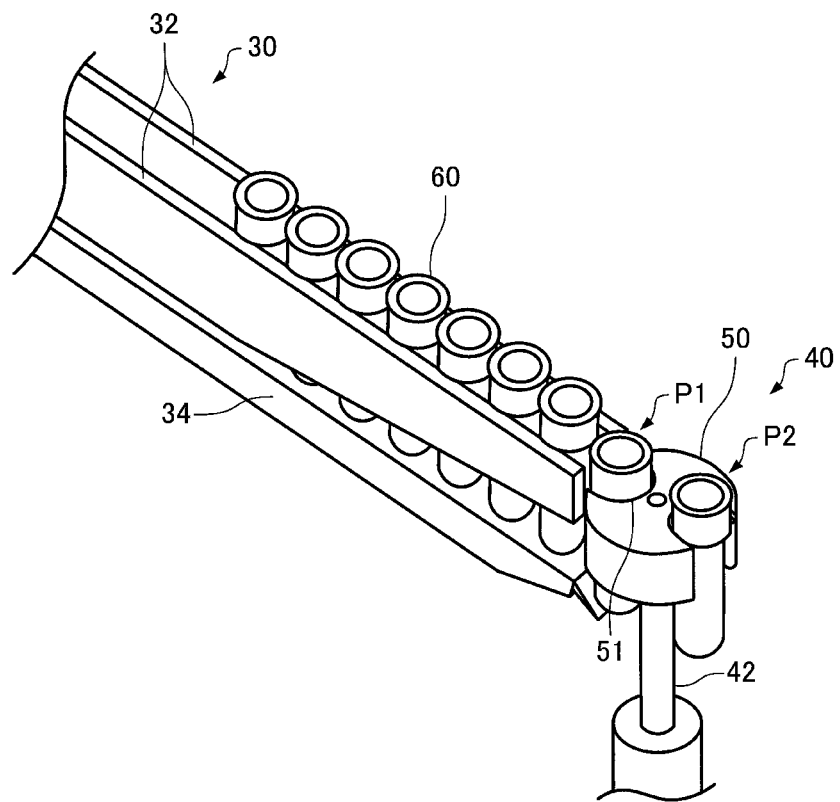
FIG. 2 is a perspective view illustrating an alignment transfer section and a supply section.

As illustrated in FIGS. 1 and 2, the alignment transfer section 30 includes a pair of alignment rails 32, an upthrust plate 34 (i.e., plate-like member) that is provided under the alignment rails 32, and a driver section that causes the upthrust plate 34 to make an upward-downward motion. The alignment rails 32 slope downward toward the end thereof (toward the supply section 40), and the upthrust plate 34 slopes so as to be parallel to the alignment rails 32. The measurement container 60 that has fallen from the belt 24 aligns along the alignment rails 32 due to its weight. The measurement containers 60 that have been aligned along the alignment rails 32 are transferred toward the end of the alignment rails 32 while making an upward-downward motion due to the upthrust motion of the upthrust plate 34. The details of the alignment transfer section 30 are described later.

The supply section 40 includes a holding section 50 that holds the measurement container 60, a support section 42 that supports the holding section 50 so as to be rotatable, and a driver section that rotates the holding section 50. The holding section 50 is provided with two holding guides 51 that can hold the measurement container 60.

The measurement container 60 that has been transferred to the end of the alignment rails 32 is fitted into the holding guide 51 that is formed at a position P1, and the holding section 50 is rotated by 180° around the vertical axis so that the measurement container 60 is transferred to a supply position P2. The measurement container 60 that has been transferred to the supply position P2 is removed by an external transfer section (e.g., arm), and transferred to another area of the automatic analyzer. A sample and a reagent are put into the measurement container 60 that has been transferred to the other area of the automatic analyzer. After completion of a predetermined process, a specific substance included in the sample is quantitatively analyzed using an optical means, a magnetic means, or a chemical means.

Note that the alignment rails 32 are provided with a sensor that detects whether or not a predetermined number of measurement containers 60 have been aligned along the alignment rails 32, and the carry-out section 20 stops operation when it has been detected that a predetermined number of measurement containers 60 have been aligned along the alignment rails 32. A sensor that detects whether or not the measurement container 60 is present at the supply position P2 is provided at the supply position P2 of the supply section 40. When it has been detected that the measurement container 60 is not present at the supply position P2, the removal operation of the external transfer section (e.g., arm) is suspended for a certain period of time, and is resumed after the measurement container 60 has been transferred to the supply position P2.

Figure 3:
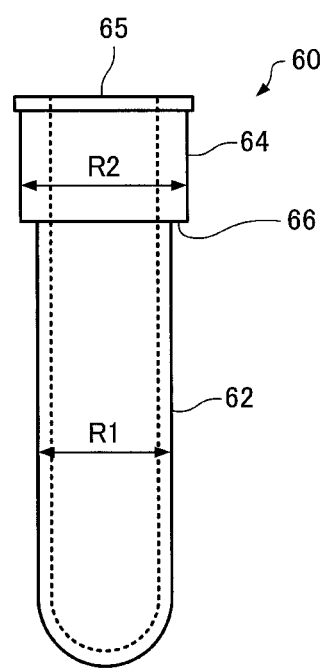
FIG. 3 is a side view illustrating a measurement container.

FIG. 3 illustrates an example of the measurement container 60. As illustrated in FIG. 3, the measurement container 60 is a container that has an approximately cylindrical shape, and has an upper opening. The measurement container 60 includes a body 62 that has an outer diameter R1, and a neck 64 that has an outer diameter R2 that is larger than the outer diameter R1. An opening 65 of the measurement container 60 is situated over the neck 64. A step 66 is formed at the interface (boundary) between the neck 64 and the body 62.

2. Configuration of Alignment Transfer Section

Figure 4:
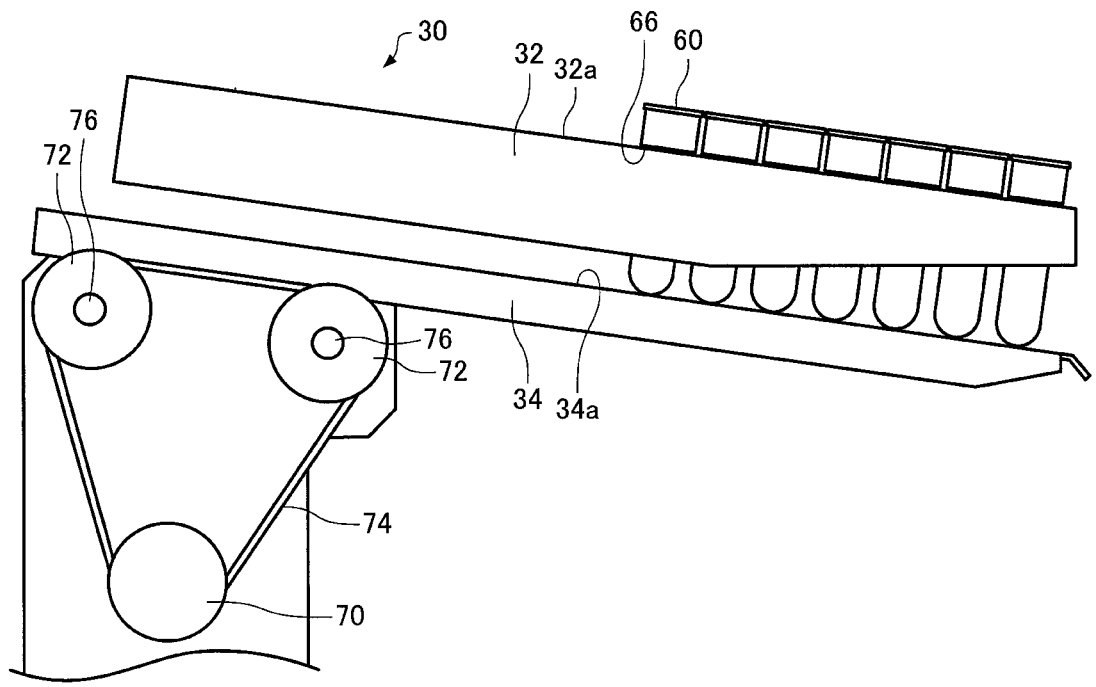
FIG. 4 is a side view illustrating an alignment transfer section.

FIG. 4 is a side view illustrating the alignment transfer section 30. As illustrated in FIG. 4, the alignment rails 32 (that make a pair) are configured so that an upper side 32a thereof comes in contact with the step 66 of the measurement container 60 to support the measurement container 60 in a suspended state. Specifically, the alignment rails 32 (that make a pair) are disposed in parallel with each other at an interval that is larger than the outer diameter R1 of the body 62 and is smaller than the outer diameter R2 of the neck 64. An upper side 34a of the upthrust plate 34 comes in contact with the bottom of the measurement container 60 that is supported by the alignment rails 32.

The alignment transfer section 30 includes a drive pulley 70, a driver section (not illustrated in FIG. 4) that rotates the drive pulley 70, two driven pulleys 72, a timing belt 74 that connects the drive pulley 70 and the two driven pulleys 72, and two eccentric shafts 76 that are respectively provided to the two driven pulleys 72, and rotatably support the upthrust plate 34. The rotational motion of the driver section (e.g., motor) is transmitted to the two eccentric shafts 76 through the drive pulley 70, the timing belt 74, and the driven pulleys 72, and converted into the upward-downward motion (vertical motion) of the upthrust plate 34.

Figure 5:
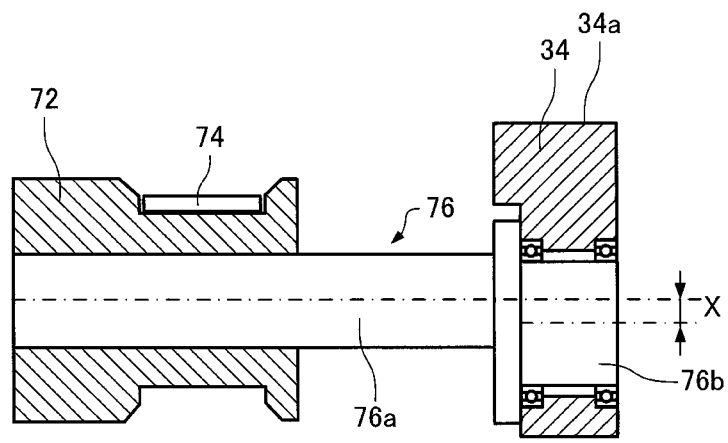
FIG. 5 is a schematic cross-sectional view illustrating an eccentric shaft.

FIG. 5 is a schematic cross-sectional view illustrating the eccentric shaft 76. As illustrated in FIG. 5, the driven pulley 72 is secured on a drive side 76a of the eccentric shaft 76, and a driven side 76b of the eccentric shaft 76 rotatably supports the upthrust plate 34 through a bearing. The driven side 76b of the eccentric shaft 76 is eccentric with respect to the drive side 76a by an eccentric amount X. Therefore, the driven side 76b produces a difference in height of 2X when the drive side 76a makes one revolution. Since the driven side 76b rotatably supports the upthrust plate 34, the upthrust plate 34 makes an upward-downward motion within the range of 2X (difference in height) when the drive side 76a makes one revolution.

Figure 6A:
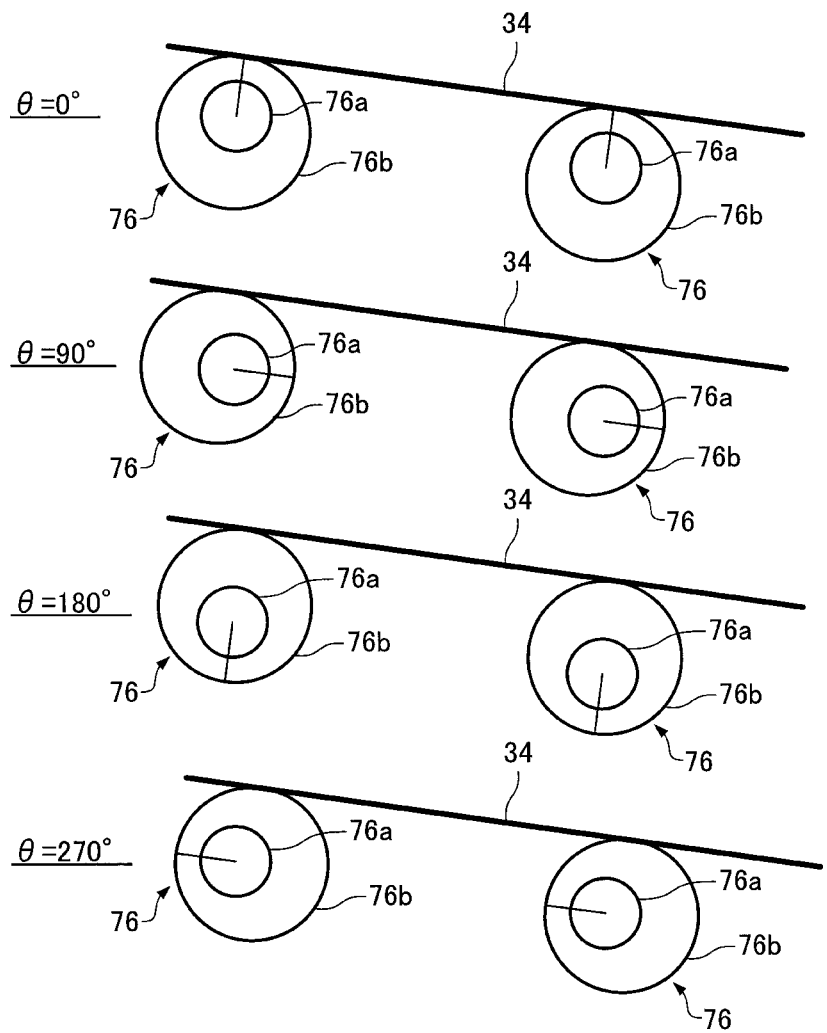
FIG. 6A is a schematic view illustrating a motion of an eccentric shaft and an upthrust plate.
Figure 6B:
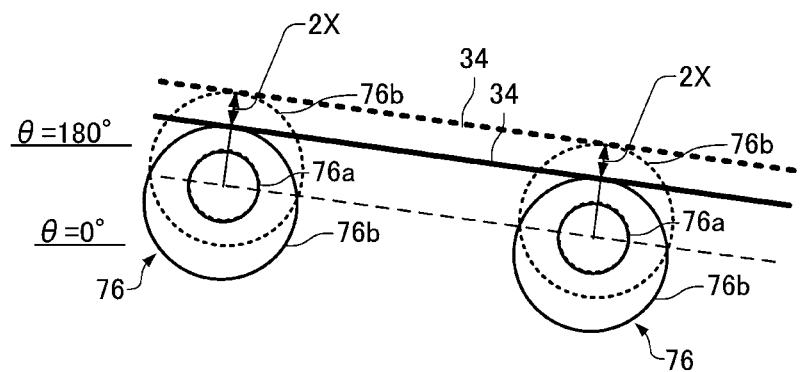
FIG. 6B is a schematic view illustrating a motion of an eccentric shaft and an upthrust plate.

FIG. 6A is a schematic view illustrating the motion of the eccentric shaft 76 and the upthrust plate 34. As illustrated in FIG. 6A, the two eccentric shafts 76 are disposed to be parallel to each other so that the rotation angle θ changes in the same phase. Therefore, the upthrust plate 34 makes an upward-downward motion (i.e., a circular motion that maintains a constant angle) while maintaining a constant slope angle when the drive side 76a of each of the two eccentric shafts 76 rotates. In FIG. 6B, the solid lines indicate the positions of the eccentric shafts 76 and the upthrust plate 34 when the rotation angle θ of the eccentric shafts 76 is 0° (or 360°), and the dotted lines indicate the positions of the eccentric shafts 76 and the upthrust plate 34 when the rotation angle θ of the eccentric shafts 76 is 180°. As illustrated in FIG. 6B, the upthrust plate 34 makes an upward-downward motion in the vertical direction (i.e., the direction orthogonal to the longitudinal direction of the upthrust plate 34) within the range of 2X (difference in height) when the eccentric shafts 76 make one revolution. Since the alignment rails 32 are secured on the device, the distance between each alignment rail 32 and the upthrust plate 34 in the vertical direction changes as the upthrust plate 34 makes an upward-downward motion.

Figure 7:
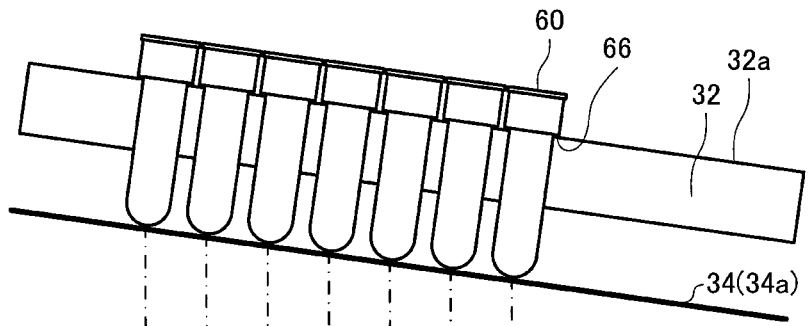
FIG. 7 is a schematic view illustrating a motion of a measurement container supported by an alignment rail.
Figure 7:
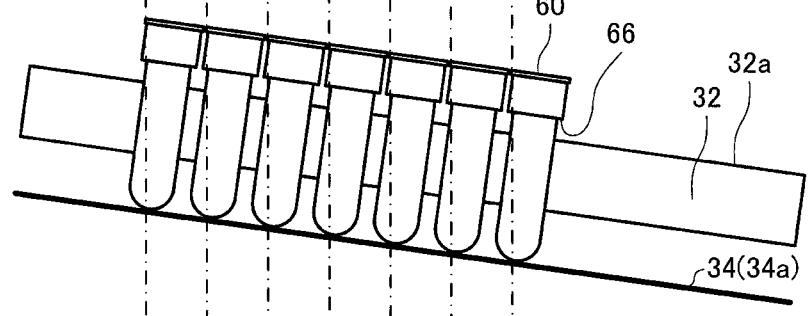
Figure 7:
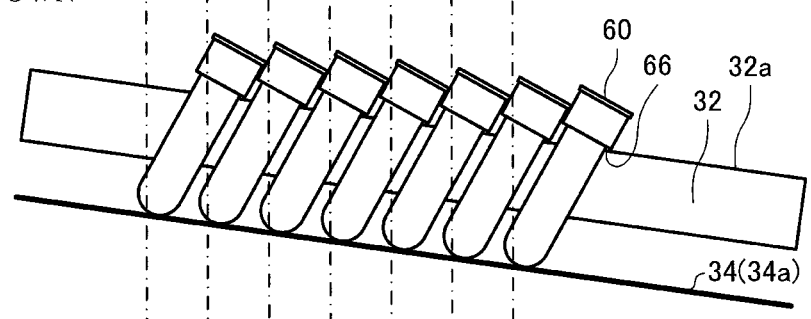
Figure 7:
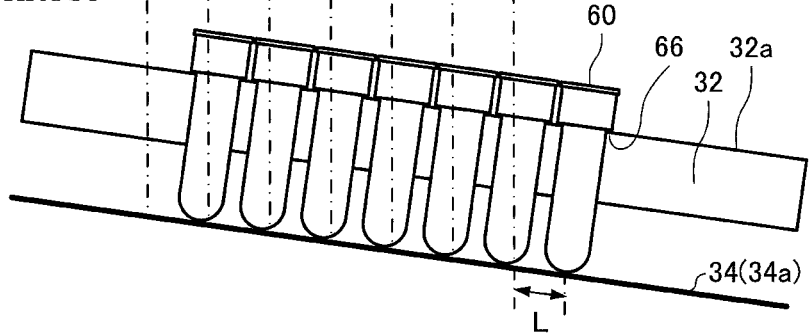

FIG. 7 is a schematic view illustrating the motion of the measurement containers 60 that are supported by the alignment rails 32. Note that FIG. 7 illustrates an example in which the upthrust plate 34 is caused to make an upward-downward motion once (i.e., the eccentric shafts 76 are caused to make one revolution) in a state in which the distance between each alignment rail 32 and the upthrust plate 34 is a maximum (i.e., a state in which the rotation angle θ of the eccentric shafts 76 is 0° in FIG. 6A) (hereinafter referred to as "start state").

In the start state illustrated in FIG. 7, the measurement containers 60 are supported by the alignment rails 32 in a suspended state in which the step 66 thereof comes in contact with the upper side 32a of each alignment rail 32, and the bottom thereof comes in contact with the upper side 34a of the upthrust plate 34.

When the upthrust plate 34 has made an upward motion (i.e., has moved upward), the measurement containers 60 are thrust upward by the upthrust plate 34 (i.e., the step 66 is situated away from the upper side 32a of each alignment rail 32). Since the alignment rails 32 slope downward toward the end thereof (i.e., toward the supply section 40 (in the rightward direction in FIG. 7)), the measurement containers 60 fall down toward the end of the alignment rails 32 (rotate clockwise around the bottom) due to their weight, and become still when the step 66 has come in contact with the upper side 32a of each alignment rail 32.

When the upthrust plate 34 has made a downward motion (i.e., has moved downward), the measurement containers 60 rotate counterclockwise around the point of contact between the step 66 and the upper side 32a of each alignment rail 32, and are supported by the alignment rails 32 in the suspended state. The measurement containers 60 thus move toward the end of the alignment rails 32 by the fall amount (moving amount L). It is possible to move the measurement containers 60 toward the end of the alignment rails 32 by repeatedly causing the upthrust plate 34 to make the above motion (upward-downward motion).

The measurement container supply device 1 according to one embodiment of the invention is thus configured so that the measurement containers 60 are transferred toward the end of the alignment rails 32 by causing the upthrust plate 34 to make an upward-downward motion so that a state in which the step 66 comes in contact with the upper side 32a of each alignment rail 32 and a state in which the step 66 is situated away from the upper side 32a of each alignment rail 32 are alternately repeated. This makes it possible to reliably transfer the measurement containers 60 along the alignment rails 32.

Although FIG. 6A illustrates an example in which the upthrust plate 34 is caused to make an upward-downward motion by rotating the eccentric shafts 76 clockwise when the alignment rails 32 slope downward in the rightward direction, the upthrust plate 34 may be caused to make an upward-downward motion by rotating the eccentric shafts 76 counterclockwise. In the example illustrated in FIG. 6A, the moving amount L of the measurement containers 60 when the eccentric shafts 76 are caused to make one revolution (i.e., the upthrust plate 34 is caused to make an upward-downward motion once) counterclockwise is larger than the moving amount L of the measurement containers 60 when the eccentric shafts 76 are caused to make one revolution clockwise. Specifically, when the upthrust plate 34 is caused to make an upward-downward motion (i.e., a counterclockwise circular motion that maintains a constant angle) by rotating the eccentric shafts 76 counterclockwise, the upthrust plate 34 pushes the bottom of the measurement containers 60 in the upper left direction while the measurement containers 60 fall down clockwise due to their weight. Therefore, the moving amount L when the eccentric shafts 76 are rotated counterclockwise is larger than the moving amount L when the eccentric shafts 76 are rotated clockwise.

3. Modifications

The invention is not limited to the above embodiments. Various modifications and variations may be made of the above embodiments. The invention includes configurations that are substantially the same as the configurations described in connection with the above embodiments (e.g., in function, method and effect, or objective and effect). The invention also includes a configuration in which an unsubstantial element described in connection with the above embodiments is replaced by another element. The invention also includes a configuration having the same effects as those of the configurations described in connection with the above embodiments, or a configuration capable of achieving the same object as those of the configurations described in connection with the above embodiments. The invention further includes a configuration obtained by adding a known technique to the configurations described in connection with the above embodiments.

Figure 8:
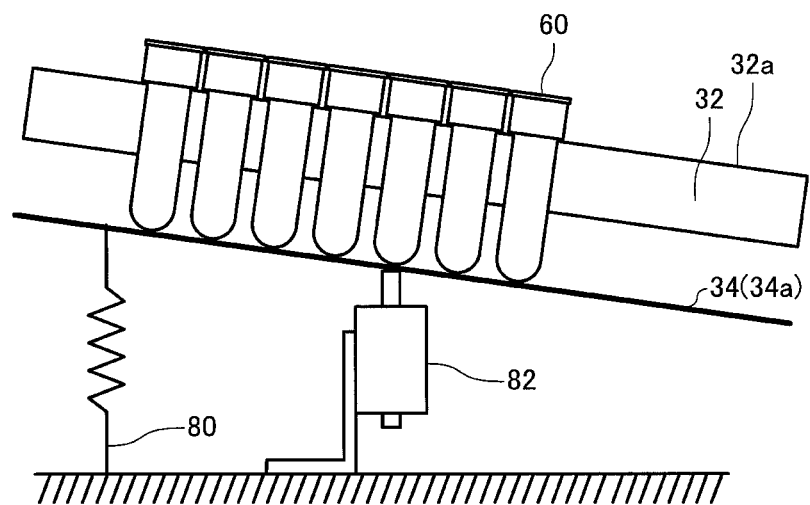
FIG. 8 illustrates a modification.

Although the above embodiments have been described taking an example in which the upthrust plate 34 is caused to make an upward-downward motion by rotating the eccentric shaft 76 that rotatably supports the upthrust plate 34 (plate-like member), the configuration is not limited thereto. As illustrated in FIG. 8, the upthrust plate 34 may be biased in the vertical direction using a tension spring 80, and a solenoid 82 may be provided under the upthrust plate 34, and cause the upthrust plate 34 to make an upward-downward motion, for example. In this case, the upthrust plate 34 is pushed upward when power is supplied to the solenoid 82, and is moved downward due the action of the tension spring 80 when the supply of power to the solenoid 82 is stopped.

Although the above embodiments have been described taking an example in which the upthrust plate 34 (plate-like member) is caused to make an upward-downward motion in a state in which the alignment rails 32 are fixed, the alignment rails 32 may be caused to make an upward-downward motion in a state in which the plate-like member is fixed. In this case, the measurement containers 60 are caused to fall down by moving the alignment rails 32 downward in the start state illustrated in FIG. 7, and the alignment rails 32 are moved upward so that the measurement containers 60 are supported by the alignment rails 32 in a suspended state. The measurement containers 60 are thus moved (transferred) forward. When the configuration in which the alignment rails 32 are caused to make an upward-downward motion is employed, the measurement container 60 that falls from the carry-out section 20 is easily fitted to the alignment rails 32, and it is possible to suppress a situation in which the measurement containers 60 are not transferred along the alignment rails 32. Alternatively, the alignment rails 32 and the upthrust plate 34 (plate-like member) may be caused to make an upward-downward motion in an opposite phase. In this case, the measurement containers 60 are caused to fall down by moving the alignment rails 32 downward while moving the upthrust plate 34 upward in the start state illustrated in FIG. 7, and the alignment rails 32 are moved upward while moving the upthrust plate 34 downward so that the measurement containers 60 are supported by the alignment rails 32 in a suspended state. The measurement containers 60 are thus moved (transferred) forward.

Figure 9:
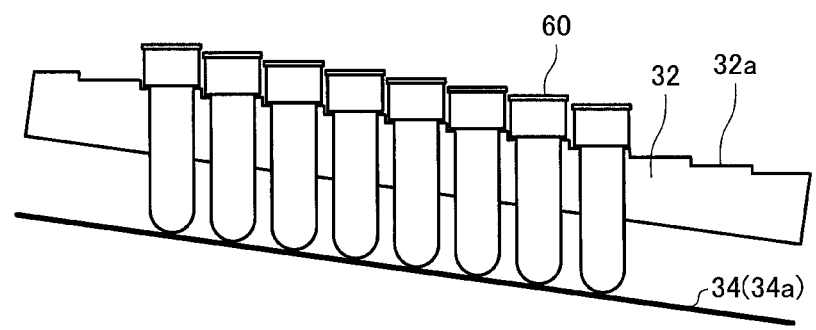
FIG. 9 illustrates another modification.

Although the above embodiments have been described taking an example in which the upper side 32a of the alignment rails 32 is flat, the upper side 32a of the alignment rails 32 may be provided with steps (i.e., may have a step-like configuration) (see FIG. 9). In this case, the measurement containers 60 move forward stepwise along the alignment rails 32 each time the upthrust plate 34 or the alignment rails 32 make an upward-downward motion. This makes it possible to maintain the posture of the measurement container 60 supported by the alignment rails 32 so that the longitudinal direction thereof is parallel to the vertical axis.

REFERENCE SIGNS LIST

1: measurement container supply device, 10: storage section, 20: carry-out section, 22: holding plate, 24: belt, 30: alignment transfer section, 32: alignment rail, 34: upthrust plate (plate-like member), 40: supply section, 42: support section, 50: holding section, 51: holding guide, 60: measurement container, 62: body, 64: neck, 65: opening, 66: step, 70: drive pulley, 72: driven pulley, 74: timing belt, 76: eccentric shaft, 80: tension spring, 82: solenoid

The invention claimed is:

1. A measurement container supply device that is included in an automatic analyzer, the measurement container supply device comprising:

a storage section that stores a measurement container;

a carry-out section that carries the measurement container out of the storage section;

an alignment transfer section that transfers the measurement container that has been carried by the carry-out section and aligned along an alignment rail toward an end of the alignment rail; and a supply section that holds the measurement container that has been transferred to the end of the alignment rail, and transfers the measurement container to a predetermined supply position, the measurement container including a body and a neck that has an outer diameter larger than an outer diameter of the body, a step that is formed by the body and the neck coming in contact with an upper side of the alignment rail so that the measurement container is supported by the alignment rail in a suspended state, the alignment rail being disposed to slope downward toward the end, and the alignment transfer section including a plate-like member that comes in contact with a bottom of the measurement container that is supported by the alignment rail, and transferring the measurement container toward the end of the alignment rail by causing at least one of the plate-like member and the alignment rail to make an upward-downward motion.

2. The measurement container supply device as defined in claim 1, wherein the alignment transfer section causes at least one of the plate-like member and the alignment rail to make an upward-downward motion so that a state in which the step comes in contact with the upper side of the alignment rail and a state in which the step is situated away from the upper side of the alignment rail are alternately repeated.

3. The measurement container supply device as defined in claim 1, wherein the alignment transfer section causes the plate-like member or the alignment rail to make an upward-downward motion by rotating an eccentric shaft that rotatably supports the plate-like member or the alignment rail.

* * * * *